(12) United States Patent
Dardai

(10) Patent No.: US 6,399,566 B1
(45) Date of Patent: Jun. 4, 2002

(54) TOPICAL PREPARATION FOR INTRODUCING INSULIN IN LIVING ORGANISMS

(75) Inventor: Zoltan Dardai, Budapest (HU)

(73) Assignee: Diabetictrust AG, Altrusried (DE)

(*) Notice: Subject to any disclaimer, the term of this patent is extended or adjusted under 35 U.S.C. 154(b) by 0 days.

(21) Appl. No.: 09/319,282

(22) PCT Filed: Sep. 8, 1997

(86) PCT No.: PCT/HU97/00049

§ 371 (c)(1),
(2), (4) Date: Jun. 3, 1999

(87) PCT Pub. No.: WO98/24470

PCT Pub. Date: Jun. 11, 1998

(30) Foreign Application Priority Data

Dec. 3, 1996 (HU) .............................................. 96 03327

(51) Int. Cl.$^7$ ............................................... A61K 38/28
(52) U.S. Cl. ................................ 514/3; 514/2; 530/330
(58) Field of Search .............................. 424/407; 514/2, 514/12, 3; 530/303

(56) References Cited

U.S. PATENT DOCUMENTS

| | | | | | |
|---|---|---|---|---|---|
| 4,508,707 | A | * | 4/1985 | Ayukama | 424/70 |
| 5,558,889 | A | * | 9/1996 | Rossi | 426/89 |
| 5,589,195 | A | * | 12/1996 | Potter et al. | 424/499 |

FOREIGN PATENT DOCUMENTS

| | | |
|---|---|---|
| DE | 30 09 143 | 10/1981 |
| WO | WO 96/15771 | 5/1996 |
| WO | WO 96/23522 | 8/1996 |

* cited by examiner

Primary Examiner—Michael Borin
(74) Attorney, Agent, or Firm—Young & Thompson

(57) ABSTRACT

The invention relates to topically applicable pharmaceutical preparations which enable one to introduce insulin in living organisms by transdermal resorption. These preparations comprise (i) insulin (ii) capsaicine, histamine and/or cantharis extract, and (iii) an epithelizing agent in admixture with carriers and/or diluents conventionally applicable in topical pharmaceutical preparations, optionally applied onto a support capable of adhering to skin.

8 Claims, No Drawings

TOPICAL PREPARATION FOR INTRODUCING INSULIN IN LIVING ORGANISMS

The invention relates to topically applicable pharmaceutical preparations which enable one to introduce peptidaceous pharmacons in living organisms by transdermal resorption. The topically applicable pharmaceutical preparations according to the invention may be e.g. ointments, creams, gels, lotions, solutions suspensions and similar formulations routinely utilized in topical treatments. Which can be applied onto the skin surface optionally in supported forms. Particularly preferred representatives of them are those wherein the topically applicable formulation is applied onto a support capable of adhering to skin, i.e. plasters (patches), which enable safe dosing and easy handling.

Topically applicable pharmaceutical preparations are outstandingly preferred formulations with respect to the treatment comfort of the patient. In contrast to parenteral formulations, like injections, the introduction of which is painful or at least unpleasant and requires either assistance of a doctor or of a nurse, or, when self-administered, requires practice and skill from the patient, a topical formulation can be applied to the place of treatment easily and painless even by the patient. Topical formulations are also more preferred than oral ones for patients who suffer from dysphagia or are averse to the taste of the medicine. A specific advantage of topical formulations is that the patient can, either at first sight or by touching his skin, easily ascertain whether he has applied the medicine or not, thereby the risk of inadvertent overdosing or underdosing considerably decreases Despite of these advantages topically applicable formulations are utilized in medical practice in a rather narrow range, generally only for the treatment of external injuries and local inflammations. The reasons of this fact lie primarily on the physiological features of active agent resorption. In order to enable a topically applied active agent to reach the target organ in an appropriate concentration the active agent should penetrate not only through the skin but also through the walls of the subdermal blood vessels. Even skin and vessel walls are of highly restricted permeability owing to their physical structures (porosity and semipermeable membrane nature). Further significant hindrance arises from the so-called barrier function of the horny layer, which latter serves essentially to protect living organisms from foreign substances contacting the skin.

There have already been elaborated some topical formulations which can successfully replace oral ones for the introduction of the active agent concerned. One of them is an antirheumatic patch marketed in Hungary since about 15 years under the name MOTTO(R), which comprises formic acid (as an antirheumatic agent) salicylic acid and optionally a pain-relieving agent in an emulsion formed with *Unguentum emulsificans* (a cream comprising nonionic tensides, Ph.Hg.V.), which is applied on a support capable of adhering to skin. NITRODERM(R), a composition sold by Ciba-Geigy Co. (German Federal Republic), comprises nitroglycerol (as a cardiac agent) in a gel formed with methyl or carboxymethyl cellulose, which is applied on small polyurethane sponges capable of adhering to skin. SALONPAS(R), a composition sold by Hisamitsu Pharmaceutical Co. Inc. (Japan), comprises methyl salicylate (as an anti-inflammatory agent) and menthol in a thick mass formed with polyvinyl alcohol, which is applied on small polyurethane sponges capable of adhering to skin. The active agents in these known compositions are strongly polar substances of relatively low molecular weights. thus they have much more chance for resorption than less polar substances with higher molecular weights.

Peptidaceous compounds form an important group of pharmaceutically active substances. In the specification and claims the term "peptidaceous compound" or "peptidaceous pharmacon" refers generally to any pharmaceutically active substance the molecule of which comprises at least two amino acids bound together by a peptide bond. A narrower group of them with outstanding pharmaceutical importance is the group of polypeptides, of which natural hormones and artificial analogues and derivatives thereof are of particular interest. A member of this latter group with outstanding importance from the aspects of public health is insuline. Hormones and hormone analogues which regulate fine balances of the organism are hazardous substances, thus with these substances it is particularly necessary to decrease the risks of inadvertent overdosing or underdosing. Some representatives of hormones and hormone analogues, in particular insuline, can be introduced only parenterally. Thus it would be highly desirable to introduce these active agents topically in the living organism. However, topical preparations applicable for introducing peptidaceous pharmacons in living organisms have not been disclosed before.

Based on my studies I have found that, upon utilizing specific auxiliary agents, peptidaceous pharmacons can be brought to a form capable of transdermal resorption. This recognition enables one to produce topically applicable pharmaceutical preparations comprising peptidaceous pharmacons Thus, the invention relates to a topically applicable preparation for introducing a peptidaceous pharmacon in a living organism. The preparation according to the invention comprises (i) a peptidaceous pharmacon,
(ii) capsaicine, histamine and/or cantharis extract. and
(iii) an epithelizing agent, in admixture with carriers and/or diluents conventionally applied in topical pharmaceutical preparations, optionally applied onto a support capable of adhering to skin.

The preparations according to the invention may comprise as peptidaceous pharmacon preferably a natural hormone or a synthetic analogue or derivative thereof, particularly preferably insuline. The amounts of peptidaceous pharmacons contained in a unit dose (i.e. in a dose for a single treatment) of the preparations according to the invention (such as in a single plaster) may be about the same as present in the conventional oral or parenteral unit dose forms. Thus, as an example, plasters according to the invention applicable in the treatment of diabetes mellitus may comprise 0.1–50 IU of insuline for one plaster or for a unit plaster fragment (e.g. for 1 $cm^2$ of plaster surface).

Capsaicine, histamine and cantharis extract (the active agent of *Tinctura cantharidis*), which form component (ii) of the preparations according to the invention, are rubefacient local vasodilators. These substances have been applied for a long time in the therapy as external rubs for stimulating subdermal circulation e.g for the treatment of chilblains, extremital pains, rheuma and the like [Kiráy, Rácz, Török: B ör- és nemibetegsegek (Skin and Venereal Diseases, in Hungarian); 1927 and subsequent pages (Medicina K önyvkiadó, Budapest, 1986)]. As epithelizing agent, which is component (iii) of the preparation according to the invention, any agent known to be applied in the therapy to loosen the upper epithelial layer of skin can be utilized. Characteristic representatives of such agents are listed e.g in the textbook cited above. Salicylic acid, sodium chloride, urea and resorcinol are examples of epithelizing agents which can be utilized with good results in the preparations according to the invention.

Although, as it appears from the textbook cited above, components (ii) and (iii) of the preparation according to the invention have already been utilized before separately in compositions for topical treatment, no data can be found in the literature on their combined use and on their prospective combined effects. No data can be found in the literature, either, that component (ii) or component (iii) would have been utilized before in combination with a peptidaceous pharmacon for the purpose of topical treatments.

In the preparations according to the invention components (i) and (ii) interact with one another, which is verified e.g. by the observation that when capsaicine is added to an insuline suspension (such as to a preparation sold by Novo Nordisk under the name Insulin lente MC), a transparent solution forms. The accurate nature of this interaction has not yet been elucidated, however, most probably hydrogen bonds are formed between the loose hydrogen-bearing groups and the local hydrogen acceptor centres of the two components (such as between the HO-and HOOC-groups of capsaicine and the—$NH_2$ groups of insuline). In my opinion the transdermal resorption ability of peptidaceous pharmacons from the preparations according to the invention can be attributed basically to this interaction.

The preparations according to the invention must contain component (ii) at least in an amount enabling the above interaction to take place, it is preferred, however, when the preparations contain more component (ii) than this minimum. For any individual peptidaceous pharmacon/component (ii) pairs the minimum and suitable ratios can be determined easily by tests belonging to the routine knowledge of one skilled in pharmacotechnology. As a guidance, e.g. insuline-containing preparations according to the invention may contain 0.001–0.3 a, preferably 0.003–0.1 g, particularly preferably 0.005–0.05 g of component (ii) for 10 IU of insuline The preparations according to the invention may contain components (ii) and (iii) in a weight ratio of 1:(0.01–10), preferably in a weight ratio of 1:(0.03–3), particularly preferably in a weight ratio of 1:(0.05–2).

I have observed that the higher is the amount of components (ii) and (iii) in the preparation according to the invention, the faster is the resorption of the active agent.

The preparations according to the invention comprise components (i)–(iii) in admixture with conventional carriers and/or diluents for topical preparations, of which the following are listed as examples: water, alcohols (also comprising glycerol), glycols, gellifying agents (such as methyl cellulose, carboxymethyl cellulose, polyvinyl alcohol and polyvinyl acetate), ointment bases (such as lanoline), ionic and monionic tenzides and the like.

The preparations according to the invention may also comprise the peptidaceous pharmacon in enveloped form (such as closed into a cyclic starch or microencapsulated). Use of such an envelope may be necessary from pharmacotechnological considerations, for instance when the peptidaceous pharmacon concerned is incompatible with the selected carriers or diluents. For instance, hydrophilic pharmacons, when closed into an envelope of hydrophobic surface, can be rendered compatible with oily carriers. In such instances the interaction between components (i) and (ii) proceeds at the rate of liberation of component (i) from the envelope.

If desired, the preparations according to the invention may also comprise other pharmaceutically active or activity-increasing agents to be introduced together with the peptidaceous pharmacon. Examples of such components are zinc compounds which are sometimes added together with insuline.

If desired, the preparations according to the invention may also comprise an indicator suitable to detect the presence of the peptidaceous pharmacon. Substances which react with a visually observable change (most suitably with a colour reaction) to the presence or absence of the pharmacon concerned can be utilized as indicators. Ninhydrine, which indicates the presence of a peptidaceous substance by blue colouration, is a very suitable indicator to show the presence of peptidaceous substances. A great advantage of such indicator-containing preparations is that the patient can easily conclude from the colour change of the applied composition (e.g. from the disappearance of the blue colour of ninhydrine) whether resorption has taken place or not, and, if necessary, can change the already exhausted plasters at due intervals. The preparations according to the invention may comprise the indicator in amounts which provide good observability. These amounts are well known to one skilled in analytics or can be determined easily by routine tests.

The following examples serve to demonstrate the composition and manufacture of the preparations according to the invention.

EXAMPLE 1

0.28 ml of Tinctura capsaicini (Ph. Hg. V. capsaicine-containing 70% alcohol solution) and 0.05 g of salicylic acid were added to 10 ml of an intramuscularly administerable aqueous suspension comprising 40 lU/mi of insuline (sold by Novo Nordisk under the trade name Insulin rapitard). Upon adding the capsaicine, a transparent solution formed from the insuline suspension. 0.01% by weight of ninhydrine were added to the solution, whereupon the colour of the solution turned blue. The resulting solution was gellified by adding 15% by weight of methyl cellulose, and the resulting gel was applied onto a polyurethane sponge plaster with an active surface of 20 $cm^2$. The gel applied was covered with aluminium foil.

EXAMPLE 2

10 g of Unguentum nonionicum emulsificans (Ph.Hg.V., an oily gel formed with nonionic tenzides) was admixed with 10 g (400 IU) of crystalline insulin, 0.05 g of crystalline salicylic acid and 0.28 ml of Tinctura capsaicini. The resulting oily ointment was applied onto a polyurethane sponge plaster with an active sur-face of 20 $cm^2$ and the ointment applied was covered with aluminium foil.

I claim:
1. A topically applicable preparation for introducing insulin in a living organism, which comprises:
   (i) insulin,
   (ii) a member selected from the group consisting of capsaicine, histamine and cantharis extract, and
   (iii) an epthelizing agent which loosens the upper epithelial layer of skin
   in admixture with a topically pharmaceutically acceptable excipient, component (ii) being present in an amount of 0.001–0.3 g for 10 IU of said insulin which, when added to an aqueous suspension of component (i), forms a solution.
2. A preparation as claimed in claim 1, which comprises 0.003–0.1 g of component (ii) for 10 IU of said pharmacon.
3. A preparation as claimed in claim 2, which comprises 0.005–0.05 g of component (ii) for 10 IU of said pharmacon.
4. A preparation as claimed in claim 1, which comprises components (ii) and (iii) in a weight ratio of 1:(0.01–10).
5. A preparation as claimed in claim 4, which comprises components (ii) and (iii) in a weight ratio of 1:(0.03–3).
6. A preparation as claimed in claim 5, which comprises components (ii) and (iii) in a weight ratio of 1:(0.05–2).
7. A preparation as claimed in claim 1, which further comprises an indicator which reacts to the presence or absence of said pharmacon by a visually observable change.
8. A preparation as claimed in claim 7, wherein said indicator is ninhydrine.

* * * * *